United States Patent
Lu et al.

(10) Patent No.: US 10,648,032 B2
(45) Date of Patent: May 12, 2020

(54) HIGH-THROUGHPUT SEQUENCING METHOD FOR METHYLATED CPG ISLAND IN TRACE DNA

(71) Applicant: SHANGHAI EPICAN GENETECH CO., LTD., Shanghai (CN)

(72) Inventors: Xingyu Lu, Shanghai (CN); Yanqun Song, Shanghai (CN)

(73) Assignee: SHANGHAI EPICAN GENETECH CO., LTD., Shanghai (CN)

( * ) Notice: Subject to any disclaimer, the term of this patent is extended or adjusted under 35 U.S.C. 154(b) by 21 days.

(21) Appl. No.: 15/993,080

(22) Filed: May 30, 2018

(65) Prior Publication Data

US 2018/0312919 A1 Nov. 1, 2018

Related U.S. Application Data

(63) Continuation of application No. PCT/CN2016/075864, filed on Mar. 8, 2016.

(30) Foreign Application Priority Data

Mar. 2, 2016 (CN) .......................... 2016 1 0119392

(51) Int. Cl.
*C12Q 1/68* (2018.01)
*C12Q 1/6874* (2018.01)
*C12Q 1/6806* (2018.01)
*C12Q 1/6827* (2018.01)

(52) U.S. Cl.
CPC .............. *C12Q 1/6874* (2013.01); *C12Q 1/68* (2013.01); *C12Q 1/6806* (2013.01); *C12Q 1/6827* (2013.01)

(58) Field of Classification Search
None
See application file for complete search history.

(56) References Cited

U.S. PATENT DOCUMENTS

2006/0110767 A1* 5/2006 Schuetz ............... C12Q 1/6886
435/6.12
2016/0298183 A1* 10/2016 Wen ..................... C12Q 1/6827

* cited by examiner

Primary Examiner — James Martinell

(57) ABSTRACT

Disclosed is a high-throughput sequencing method for methylated CpG island in trace DNA, comprising the steps of: 1) treating a DNA sample with bisulfite; 2) adding the treated sample obtained in step 1) to a PCR system containing a primer A for linear amplification; 3) adding an exonuclease having single-stranded DNA cleaving activity to the PCR product in step 2) and inactivating the exonuclease after the reaction; 4) adding the product in step 3) to a PCR system containing a primer B for linear amplification; 5) adding the product in step 4) to a PCR system containing the corresponding adapter primer C and adapter primer D for amplification; and 6) purifying the PCR product in step 5) to obtain a DNA library with a specific length and carrying out the sequencing.

9 Claims, No Drawings
Specification includes a Sequence Listing.

HIGH-THROUGHPUT SEQUENCING METHOD FOR METHYLATED CPG ISLAND IN TRACE DNA

CROSS-REFERENCE TO RELATED APPLICATIONS

This application is a continuation of International Patent Application No. PCT/CN2016/075864 with a filing date of Mar. 8, 2016, designating the United States, and further claims priority to Chinese Patent Application No. 201610119392.2 with a filing date of Mar. 2, 2016. The content of the aforementioned application, including any intervening amendments thereto, are incorporated herein by reference.

TECHNICAL FIELD

The disclosure relates to high-throughput sequencing method for methylated CpG Island in trace DNA, and belongs to the field of gene sequencing.

TECHNICAL BACKGROUND

DNA methylation is an important modification of DNA base. It mainly refers to the covalent modification of methylation on the number 5 carbon atom of cytosine, which is basically present in the DNA of all species. Methylation modification of cytosine exists in the special structure of CpG and appears in pairs in the double-stranded DNA; in the vertebrate structural genome, most of the CpG structural domains are mainly concentrated in the gene promoter region, and methylation occurs on cytosine in 60%-90% of CpG regions. Methylation of DNA can lead to changes in DNA conformation, stability, interaction mode between DNA and protein, and the structure of chromatin, which in turn affects the regulation of gene expression, and thus plays an enormous role in cell development and differentiation, the expression of characteristic phenotypic genes, and X chromosome inactivation, and etc. Therefore, accurate sequencing of DNA methylation sites in the genome is an important part of a comprehensive understanding of the characteristics and functions of genes.

Traditional single-point methylation detection or sequencing methods (eg, restriction enzyme digestion, restriction enzyme digestion-PCR, methylation-specific PCR, pyrosequencing, fluorescent quantitation etc.) can only detect single or multiple sites once due to limitation in the technical method, and the method is complicated; genomic methylation map can be drawn based on the methylation map of the chip, but the method is required in a smaller amount, and the cost is higher, which is not suitable for large-scale use. With the development of second-generation sequencing methods in recent years, people can further systematically and accurately understand the distribution of methylation in the genome by high-throughput sequencing method. Currently, there are three types of methylation sequencing methods based on high-throughput sequencing: (1) immunoprecipitation; (2) bisulfite sequencing; and (3) methylated CpG random amplification and sequencing methods (MCTA-Seq). The immunoprecipitation method requires the purchase of antibodies with specific recognition effects, and this sequencing method can only be regarded as semi-quantitative, with a resolution of only about 100 bp. The bisulfite sequencing method is accurate to single base and is the gold standard for methylation analysis. In this method, the DNA sample is treated with bisulfite and the unmethylated cytosine is converted into uracil. Then, the promoter and CpG island region are enriched through enzyme digestion, gel purification, and etc, and the library is further established and sequenced; however, the method comprises complicated procedures and is time-consuming, costly and the cost performance is low, thus it does not have wide applicability. The method for random amplification and sequencing of methylated CpG is an improved method based on bisulfite method. In the method, the collected DNA samples are treated with bisulfite to obtain converted samples, and then CpG-enriched methylation regions (especially CpG island regions) are amplified through specific primers and DNA libraries are created. Then, the target region fragment is enriched by way of cutting the gel, and then the methylated CpG island sequencing analysis in a specific region is realized. This method can reduce the cost and effectively cover more than 80% of the CpG island region. It is of great significance for the analysis of DNA methylation distribution. However, this method still has three major defects: 1) the obtained DNA library always contains extremely large number of primer dimers and impurities, plus the limitations of the bisulfite sequencing method, the actual sequencing effect is greatly disturbed, thus the cost of sequencing is increased; 2) the range of CpG islands that can be captured by primers still cannot cover all the promoter regions; 3) the steps of library construction and purification of this method still rely heavily on the judgment and skills of the operators, which is disadvantageous to automated industrial operation.

There is currently a lack of a more efficient commercial high-throughput sequencing method for methylated CpG island.

SUMMARY

The object of the present disclosure is to provide high-throughput sequencing method for methylated CpG island in trace DNA.

The present disclosure adopts the following technical solutions:

A method for high-throughput sequencing of methylated CpG island in trace DNA, comprising the following steps:
1) performing a bisulfite treatment on the obtained trace amount of DNA sample to obtain a single-stranded DNA sample converted with bisulfite;
2) adding the processed sample obtained in step 1) to a PCR system containing a primer A and linearly amplifying the processed sample obtained in step 1) in a PCR instrument;
3) adding an exonuclease having single-stranded DNA cleavage activity to the PCR product in step 2) and reacting therewith at 37° C. for 30 minutes, and then increasing the temperature to inactivate the exonuclease;
4) adding an enzyme digestion product in step 3) to the PCR system containing a primer B for linear amplification;
then adding a PCR product system in step 4) to the PCR system containing a corresponding adapter primer C and an adapter primer D for PCR amplification;
size-selective purificating a PCR product in step 5) to obtain a DNA library with a specific length, and performing high-throughput sequencing after passing the quality control required by the sequencer.

Further, the method of high-throughput sequencing for methylated CpG island in DNA according to the present disclosure can also have the following features: wherein, the 5' sequence of the primer A can be annealed to the sequencing universal adapter primer C (not limited to illumina, ion proton, roche454, solid, BGIseq); the primer A has 5-15 specific sequences at the 3' end which can be annealed to multiple CpG regions (at least two CpGs).

Further, the method for high-throughput sequencing of methylated CpG island in trace DNA according to the present disclosure can also have the feature that the 5' sequence in the primer B can be annealed to the adapter primer D.

Further, the method for high-throughput sequencing of methylated CpG island in trace DNA according to the present disclosure may also have the feature that the 3' sequence of the primer B includes a relatively random annealing sequence having 5-15 bases in length; this sequence contains 0-15 bases C, 0-15 bases D, and 0-7 CpG.

Further, the method for high-throughput sequencing of methylated CpG island in trace DNA according to the present disclosure may also have the feature that the first base at the 3' end of the primer B is D (mixture of A, T, and G), and the immediate second and third bases are one CpG enrichment zone, while the 4th-9th bases contain one base C, and the other bases are D (A, T, G).

Further, the method for high-throughput sequencing of methylated CpG island in the DNA of the present disclosure may further have the feature that the 5' sequence and the 3' sequence of the primer are linked by 4 to 20 bases D (mixture of A, T, G).

Further, the method for high-throughput sequencing of methylated CpG island in DNA of the present disclosure may also have the following feature: the primer B may be a single primer, or a mixture of multiple primers;

Further, the method for high-throughput sequencing of methylated CpG island in the DNA of the present disclosure may also have the following feature: wherein, the primer B is a mixture of the following four primers:

5'-GTGACTGGAGTTCAGACGTGTGCTCTTC-CGATCTCATGDDDDDDDDG CGD-3' (SEQ NO: 2); wherein, D is A or T or G.

5'-GTGACTGGAGTTCAGACGTGTGCTCTTC-CGATCTCATGDDDDDDDGD CGD-3' (SEQ NO: 3); wherein, D is A or T or G.

5'-GTGACTGGAGTTCAGACGTGTGCTCTTC-CGATCTCATGDDDDDDGDD CGD-3' (SEQ NO: 4); wherein, D is A or T or G.

5'-GTGACTGGAGTTCAGACGTGTGCTCTTC-CGATCTCATGDDDDDGDDD CGD-3' (SEQ NO: 5); wherein, D is A or T or G.

Further, the method for high-throughput sequencing of methylated CpG island in the DNA of the present disclosure can also have the following feature: the sequence of the primer C is as follows:

(SEQ ID NO: 7)
5'-AATGATACGGCGACCACCGAGATCTACACTCTTTCCCTACACGACGC

TCTTCCGATCT-3'.

Further, the method for high-throughput sequencing of methylated CpG island in the DNA of the present disclosure may also have the following feature: the sequence of the primer D is as follows:

(SEQ ID NO: 6)
5'-CAAGCAGAAGACGGCATACGAGATCTGATCGTGACTGGAGTTCAGAC

GTGTGCT-3'.

In the above step 1), the source of sample of the trace amount of DNA is not limited to trace amounts of DNA sample extracted from tissues, blood, cells, body fluids, secretions, etc., in humans, animals, plants, microorganisms, etc.; the DNA extraction method is not limited to the existing phenol chloroform, column recovery and magnetic beads purification, etc.;

In the above step 1), the bisulfite treatment kit is not limited to self-contained or existing commercial bisulfite treatment kits such as Zymo EZ Methylation-Direct Kit, EpiTect Bisulfite Kits, Methylamp Whole Cell Bisulfite Modification Kit, EpiGnome™ Methyl-Seq Kit, etc.;

In the above step 2), the DNA polymerase is preferentially the hot-start DNA polymerase but is not limited to the hot-start DNA polymerase, such as: HS EX Taq DNA polymerase, Pfu polymerase, Taq DNA polymerase, hot-start Taq DNA polymerase, Phusion Polymerase, OneTaq® Hot-Start DNA Polymerase, OneTaq® DNA Polymerase, VentR® DNA Polymerase, VentR (exo-) DNA Polymerase, Deep VentR™ DNA Polymerase, Deep VentR (exo-) DNA polymerase etc.;

In the above step 2), the 5' sequence of the primer A may be annealed to the sequencing universal adapter primer C (not limited to illumina, ion proton, roche454, solid, BGIseq); the primer A has 5-15 specific sequences at the 3' end which can be annealed to multiple CpG regions (at least two CpGs); the parts linking the 5' and 3' ends of the primers are 3 to 7 H bases in length (A, T, and G mixtures). For example, the sequence of Primer A can be:

(SEQ ID NO: 1)
5'-TTTCCCTACACGACGCTCTTCCGATCTCATGHHHHCCGCGCG-3'.

In the above step 3), the source of single-stranded cleavage exonuclease is not limited to specific bacterial strain, such as exonuclease I, exonuclease II;

In the above step 5), the 5' sequence in the primer B can be annealed to the adapter primer D; the 3' sequence will include a relatively random annealing sequence having 5 to 15 bases in length, and this sequence contains 0-15 base C, 0-15 bases D and 0-7 CpG. The first base at the 3' end is D (mixture of A, T, and G), the immediate second and the third bases are a CpG enrichment zone, and the 4th to 9th bases contain a base C, and the other bases are D (A, T, G); the 5' and 3' sequences of the primers are connected by 4-20 bases D (A, T and G mixtures); the primers can be used individually or mixed with multiple primers of the same length;

In the above step 5), the DNA polymerase is preferably a DNA polymerase having a strand displacement effect but is not limited thereto. For example: Klenow (exo), phi29 DNA polymerase, Bst DNA polymerase, large fragment, Bst 2.0 DNA polymerase etc.;

In the above step 6), the adapter primer C and the adapter primer D in the PCR system can be annealed to 5' sequences of the primers A and B, respectively; the DNA polymerase is preferentially the hot start DNA polymerase but is not limited to the Hot Start DNA polymerase: such as HS EX Taq DNA polymerase, Pfu polymerase, Taq DNA polymerase, hot start Taq DNA polymerase, Phusion polymerase, OneTaq® hot start DNA polymerase, OneTaq® DNA polymerase, VentR® DNA polymerase, VentR (exo-) DNA polymerase, Deep VentR™ DNA polymerase, Deep VentR (exo-) DNA polymerase, etc.;

In the above step 7), the purification method of the PCR system is not limited to the methods of gel extraction and magnetic bead purification etc. for screening the size of the DNA fragments;

In the above step 7), high-throughput sequencing platforms include, but are not limited to, Hiseq, Miseq, NextSeq, and other sequencing platforms from Illumina company; PGM platform from Ion proton; GS Junior and GS FLX+ platforms from Roche 454 etc.;

There is no limit to the data analysis method.

Beneficial Effects

Compared with the prior art, the technology of the present disclosure adopts a multi-step PCR method to directly enrich methylated CpG island sequences in trace DNA for high-throughput sequencing of the target fragments, and it has high pertinence of DNA sequence, very high efficiency, so that it can avoid the waste of data in the sequencing process; and it can directly capture and enrich an extremely trace amount of DNA sources and establish a DNA library with high accuracy, and thus it greatly expand the application range of methylation sequencing, such as high throughput sequencing of trace DNA in blood, body fluids, and urine.

Compared with the prior art, this technique uses a single-stranded cleavage exonuclease to remove primers in multiple direct PCR systems during PCR, greatly reducing the background in the reaction system;

Compared with the prior art, the PCR technology in steps 2 to 6 of the present technology can be performed continuously in a single tube, which can avoid waste in the intermediate purification steps, saving time and labor, and can be equipped with automated equipment to complete all processes, and the quality can be improved. Under the controlled conditions, the complexity of the establishment of the DNA library is greatly optimized, the production process is simplified, and the production cost is reduced.

DETAILED DESCRIPTION

Hereinafter, specific embodiments of the present disclosure will be described.

Example 1: Establishment of a High-Throughput Sequencing Library of Methylated CpG Island in Plasma Circulating Free DNA EDTA anticoagulating blood collection tube is used to draw 1-10 ml blood from the human body, after two rounds of 1350 g centrifugation at 4° C., centrifugation time of 12 minutes, collecting the upper liquid each round, and using 13500 g high-speed centrifugation, centrifugation time of 12 minutes, to completely remove blood cells that may be present in the plasma. Immediately afterwards, the circulating free DNA is extracted from the plasma using a commercially available kit Zymo EZ Methylation-Direct Kit and eluted with an appropriate volume (20 µl), and the total amount of DNA is 1-10 ng. Sample amount below 100 ng can be called trace amount. The bisulfite treatment of the DNA system is performed immediately using a commercially available bisulfite kit to convert the cytosine that has not been modified at 5' position in the DNA to uracil while retaining the 5'-methyl-modified cytosine in the DNA sequence. Finally, the converted sample is eluted into a 10.25 µl system.

The converted DNA sample is firstly subjected to a PCR system containing primer A, and the PCR system is 15 µl in total. After the first round of PCR linear amplification, the excess primer A in the system is digested with exonuclease I (0.5 µl, 30 min); at the end of the reaction, under high temperature conditions (80° C., 20 minutes), the exonuclease I is inactivated to avoid interference to subsequent reactions. Immediately afterwards, the PCR reaction system containing the primer B is added directly in multiple steps into the reaction tube (20 µl in total), and a second round of linear amplification is performed in the PCR instrument. The third PCR reaction system containing the adapter primer C and the adapter primer D is added directly to the obtained sample tube (50 µl in volume) and subjected to exponential amplification in a PCR instrument for 18 to 22 cycles. A 45 microliter system is pipetted from the final sample in PCR tube, and the commercially available magnetic beads for size selection are used to perform multi-step purification to obtain a DNA library with a size of 190 bp to 300 bp. After the obtained DNA library passes quality inspection, high-throughput sequencing is performed and data is analyzed finally.

The specific steps for the bisulfite treatment of trace DNA samples and subsequent library construction and analysis are as follows:

1.1 Adding 790 µL M-Solubilization buffer and 300 µL M-Dilution Buffer to the CT Conversion Reagent tube; mixing the sample with vigorous shaking for 15 seconds at room temperature, then mixing with a DNA rotary mixer for 10 min;

1.2 Adding an additional 160 µL M-Reaction Buffer to the system and mixing for an additional 1 min (the final solution is clear, but slightly precipitated);

1.3 Taking 20 µL cfDNA sample (the balancing is water) in a 1.5 mL low-adsorption centrifuge tube, then adding 130 µL CT Conversion Reagent into the tube, pipetting and mixing uniformly, and transferring it into the PCR tube;

1.4 The PCR tube is placed on a PCR thermocycler and the following preliminary reactions are performed according to the following thermal cycles: 98° C., 8 min; 64° C., 3.5 h; 4° C., incubation;

1.5 Adding 600 µL M-Binding Buffer to Zymo-Spin™ IC Column, adding 1 µL Carrier RNA and putting the Column into Collection Tube;

1.6 The solution obtained from the PCR preliminary reaction is added to the Column containing the M-Binding Buffer, covered with the Column's lid and inverted 6 times;

1.7 The Column is placed on a centrifuge and centrifuged at 10000 g for 30 s and the filtrate is discarded;

1.8 100 µL M-Wash Buffer is added to the Column and centrifuged at 14000 rpm for 30 s.

1.9 200 µL M-Desulphonation Buffer is added to the Column and allowed to stand for 15-20 minutes at room temperature (20° C.-30° C.). Immediately afterwards, it is centrifuged with centrifugal force of 14000 rpm for 30 seconds.

1.10 200 µL M-Wash Buffer is added to the Column and centrifuged on a centrifuge at 14000 rpm for 30 s; and 200 µL M-Wash Buffer is added repeatedly and centrifuged with centrifugal force of 14,000 rpm for 60 s.

10) The Column is added to a new 1.5 mL low-adsorption centrifuge tube and 12.5 µL of Low TE is added. After standing at room temperature for 60 s, the DNA sample is eluted with centrifugal force of 14,000 rpm for 60 s.

In step 2, the treated sample obtained in step 1 is added to the PCR system containing the primer A.

The processed sample obtained in Step 1 is added to a PCR system containing primer A (containing a hot-start DNA polymerase) and linearly amplified in a PCR instrument.

2.1 Transferring the eluate from step 1 (11.2 µl, the balancing is DNase-free ddH$_2$O) to the PCR tube and adding in the PCR amplification system according to the following table 1. This step is performed on ice and mixed uniformly using a pipette.

TABLE 1

| Reagent or sample | Volume (µl) |
|---|---|
| DNA Sample | 11.2 |
| Primer A* | 0.5 |
| dNTP | 1.5 |
| Ex Taq buffer | 1.5 |
| Ex HS Taq (Takara) | 0.3 |
| Total | 20.0 |

Note:
*The sequence of primer A is 5'-TTTCCCTACACGACGCTCTTCCGATCT-CATGHHHHCCGCGCG-3' (SEQ ID NO: 1) (H = A/C/T) at a concentration of 5 µM.

2.2 The PCR system is placed on the PCR instrument and the first round of linear amplification is performed according to the following temperature change: 95° C., 3 min (first time); 95° C., 30 s; 50° C., 2 min; 72° C., 1 min; 4° C., incubation;

Step 3, adding exonuclease to the PCR product in Step 2 to remove the single-stranded primer in the system;

3.1 Removing the sample tube from the PCR instrument and place it on ice;

3.2 Adding 0.5 µL exonuclease I (NEB) directly to the system and mixing by pipetting.

3.3 The PCR tube is placed on PCR instrument and operated according to the following temperature change: 37° C., 30 min; 80° C., 20 min; 4° C., incubation;

Step 4, the enzyme digestion product in step 3 is added to the PCR system containing primer B and subjected to linear amplification;

4.1 Removing the PCR sample tube from the PCR instrument and adding 1.0 µL of primer B (mixture) directly and mixing by pipetting.

**: Primer B is a mixture. The concentration of mixed primers is 5.0 µM, each is 1.25 µM. The sequence thereof is as follows:

```
                                              (SEQ ID NO: 2)
5'-GTGACTGGAGTTCAGACGTGTGCTCTTCCGATCTCATGDDDDDDDG

CGD-3';
(D = A/T/G)

(SEQ ID NO: 3)
5'-GTGACTGGAGTTCAGACGTGTGCTCTTCCGATCTCATGDDDDDDDGD

CGD-3';
(D = A/T/G)

(SEQ ID NO: 4)
5'-GTGACTGGAGTTCAGACGTGTGCTCTTCCGATCTCATGDDDDDDDGDD

CGD-3';
(D = A/T/G)

(SEQ ID NO: 5)
5'-GTGACTGGAGTTCAGACGTGTGCTCTTCCGATCTCATGDDDDDGDDD

CGD-3';
(D = A/T/G)
```

4.2 Preheating the PCR instrument to 95° C., quickly inserting the sample tube into the PCR instrument and holding for two minutes, quickly removing the sample tube and inserting it into the ice water bath and holding for 3 minutes;

4.3 Preparing the second round of PCR amplification mixture system according to the following table 2;

TABLE 2

| Reagent | Volume (µl) |
|---|---|
| NEBuffer 2 | 0.5 |
| Klenow (exo) | 0.5 |
| ddH$_2$O | 3.0 |
| Total | 4.0 |

4.4 Taking 4.0 µl of the PCR amplification system into the PCR sample tube and mixing it by pipetting. Operation is performed on ice.

4.5 Pre-cooling the operating temperature of the PCR instrument to 4° C. and placing the sample tube into the instrument well. A second round of amplification is then performed according to the following temperature change: 4° C., 50 s; 10° C., 1 min; 20° C., 4 min; 30° C., 4 min; 37° C., 4 min; 75° C., 20 min; 4° C., forever***;

***: The temperature increase rate is 1° C./s at each temperature change.

Step 5, the PCR product in step 4) is purified with magnetic beads;

5.1 Removing Beckman's Ampure XP magnetic beads from 4° C., and placing it at room temperature for 15 minutes, shaking and mixing;

5.2 Drawing 20 µl of magnetic beads and adding into the sample tube, mixing with a pipette, and standing for 10 min at room temperature;

5.3 Putting the sample tube on the magnetic rack for 5 minutes, and the magnetic beads are all adsorbed on the wall of the sample tube near the magnetic rack; 80% ethanol solution is fresh formulated before use;

5.4 Opening the sample tube, using a pipette to suck out and discard all the liquid in the tube;

5.5 Using a pipette to add 200 µl of 80% ethanol solution to the tube, and letting it stand for 30 s, sucking out the ethanol solution in the tube; repeating this operation, and finally using a 10 µl pipette to completely suck out the liquid in the tube;

5.6 The sample tube is opened at room temperature for 5 minutes to allow the ethanol in the tube to evaporate completely;

5.7 Taking down the sample tube from the magnetic rack, adding 40.0 µl of ddH$_2$O to the tube to mix with the magnetical beads on the tube wall by pipetting and letting it stand for 5 min;

5.8 Placing the sample tube on the magnetic rack and holding it for 5 minutes so that the magnetic beads are completely attached to the wall of the sample tube, then transferring 38.5 µl of the sample liquid into a new PCR tube;

Step 6, the PCR product in step 5 is further added to the PCR system containing the corresponding adapter primer C and adapter primer D for PCR amplification for 15 to 25 cycles.

6.1 PCR system mixture is prepared according to the following table 3:

TABLE 3

| Reagent or sample | Volume (µl) |
|---|---|
| DNA Sample | 38.5 |
| Primer C**** | 0.5 |
| Primer D***** | 0.5 |
| dNTP | 5.0 |

TABLE 3 -continued

| Reagent or sample | Volume (μl) |
| --- | --- |
| Ex Taq buffer | 5.0 |
| Ex HS Taq (Takara) | 0.5 |
| Total | 50.0 |

\*\*\*\*the concentration of Primer C is 50 μM and the sequence is as follows: 5'-AATGATACGGCGACCACCGAGATCTACACTCTTTCCCTACAC-GACGCTCTTCCGAT CT-3' (SEQ ID NO: 6)
\*\*\*\*\*the concentration of Primer D is 50 μM and the sequence is as follows: 5'-CAAGCAGAAGACGGCATACGAGATCTGATCGTGACTGGAGTTCA-GACGTGTGCT-3' (SEQ ID NO: 7)

6.2 The above prepared PCR system is placed on a PCR instrument, and the third round of exponential amplification is performed according to the following temperature change, and the reaction is performed for 15 to 25 cycles: 95° C., 3 min (first time); 95° C., 30 s; 65° C., 30 s; 72° C., 1 min (n cycles); 4° C., forever;

Step 7, the PCR product in step 6) is purified with magnetic beads to obtain a DNA library with a specific length (DNA fragment has 200-350 bp in size), and the high throughput sequencing is carried out after passing the quality control required by the sequencer.

7.1 15 minutes before the end of the PCR reaction, taking out the Ampure XP magnetic beads and placing it at room temperature and shaking vigorously and mixing it;

7.2 After the end of PCR, taking out the sample tube, and pipetting 45.0 μl of the sample therefrom into a new PCR reaction tube, adding 31.5 μl of Ampure XP magnetic beads to the reaction tube and mixing them with a pipette and letting them stand at room temperature for 10 min.

7.3 Placing the reaction tube on a magnetic rack and letting it stand for 5 minutes to completely adhere the magnetic beads in the tube onto wall, and then pipetting and transferring 74 μl of the supernatant to a new PCR reaction tube.

7.4 adding 13.2 μl of Ampure XP magnetic beads to the new reaction tube, and mixing them with a pipette and letting them stand at room temperature for 10 minutes again;

7.5 Placing the reaction tube on a magnetic rack and letting it stand for 5 minutes to completely adhere the magnetic beads in the tube onto wall. Preparing the fresh 80% ethanol solution;

7.6 Opening the sample tube, using a pipette to suck out and discard all the liquid in the tube;

7.7 Using a pipette to add 200 μl 80% ethanol solution to the tube, and letting it stand for 30 s, sucking out the ethanol solution in the tube; repeating this operation, and finally using a 10 μl pipette to completely suck out the liquid in the tube;

7.8 Opening the sample tube and letting it stand at room temperature for 5 minutes to allow the ethanol in the tube to evaporate completely.

7.9 Taking down the sample tube down from the magnetic rack, and adding 20.0 μl of Low TE (0.1 mM EDTA, 10 mM Tris-HCl, pH=7.5) thereto. Pipetting and mixing the magnetic beads on the tube wall with a pipette again and letting them stand for 5 minutes;

7.10 Placing the sample tube on a magnetic rack and holding it for 5 minutes to make the magnetic beads thoroughly adhere to the wall of the sample tube; then, drawing 17.0 μl of the liquid to determine the concentration, thus obtaining a high-throughput sequencing library;

7.11 Using Agilent Bioanalyser_2100 analysis system to identify the size of the DNA fragments obtained from the library.

7.12 Carrying out high-throughout sequencing of the analyzed libraries on Illumina Hiseq 2500 or Illumina Hiseq X10 system platforms using pair-end sequencing method to obtain high-throughput sequencing data;

Step 8, the sequencing data in step 7 is analyzed to obtain the data information of the desired methylated CpG island and used in scientific research or medical diagnosis etc. The specific steps are as follows:

8.1 Sequencing data are initially processed to remove the adapter primers; then the acquired high-throughput sequencing data is mapped to human genome data (such as Hg19) using the data analysis software Biomark;

8.2 Deep bioinformatics analysis of the distribution of methylated CpG islands is performed.

Example 2: Establishment of High-Throughput Sequencing Library for Methylated CpG Island in DNA from Urine The first urine in the morning (100 ml to 500 ml in volume) is collected from human directly using a medical urine collector and 13500 g of high-speed centrifugation (12 minutes) is used to completely remove any possible cellular and precipitated impurities in the urine. Immediately afterwards, the circulating free DNA is extracted from the urine using a commercial kit and eluted with an appropriate volume (20 μl) (the total amount of DNA is 1-10 ng). Then, the bisulfite treatment of the DNA system is then performed using a commercial bisulfite kit to convert the cytosine that has not undergone the 5-position modification to uracil in the DNA while retaining the 5'-methyl-modified cytosine in the DNA sequence. Finally, the transformed sample is eluted into a 10.25 μl system.

The transformed DNA sample is first subjected to the first round of PCR linear amplification using the PCR system containing primer A (15 μl in total) and excess primer A in the system is digested by Exonuclease I (0.5 μl, 30 min); at the end of the reaction, the Exonuclease I is inactivated under high temperature condition (80° C., 20 minutes) to avoid interference of this enzyme to subsequent reactions. Immediately afterwards, the PCR reaction system containing the primer B is added directly to the reaction tube in multiple steps (20 μl in total), so that the second round of linear amplification is performed in the PCR instrument. The third PCR reaction system containing the adapter primer C and the adapter primer D is added directly to the obtained sample tube (50 μl in volume) and subjected to exponential amplification in a PCR instrument for 18 to 22 cycles. From the final PCR tube sample, a 45 microliter system is pipetted, commercially available magnetic beads are used for multi-step size-selection purification to obtain a DNA library with a size of 190 bp to 300 bp. After the obtained DNA library passes quality inspection, high-throughput sequencing is performed and finally data analysis is performed.

In the present embodiment, the steps of bisulfite treatment of DNA and subsequent library construction and sequencing are the same as those of the first embodiment.

The invention claimed is:

1. A method for high-throughput sequencing of methylated CpG island in trace DNA, comprising the following steps:
   1) performing a bisulfite treatment on a trace amount of DNA sample to obtain a single-stranded DNA sample converted with bisulfite;
   2) adding the sample obtained in step 1) to a PCR system containing a primer A and linearly amplifying the processed sample obtained in step 1) in a PCR instrument;
   3) adding an exonuclease having single-stranded DNA cleavage activity to a PCR product obtained in step 2) and reacting therewith at 37° C. for 30 minutes, and then increasing the temperature to inactivate the exonuclease;
   4) adding an enzyme digestion product in step 3) to a PCR system containing a primer B for linear amplification;
   5) then adding a PCR product system in step 4) to a PCR system containing a corresponding adapter primer C and an adapter primer D for PCR amplification;
   6) size-selectively purificating a PCR product in step 5) to obtain a DNA library with a specific length, and performing high-throughput sequencing after passing quality control required by a sequencer,
   wherein the first base at the beginning of the 3' portion of the primer B is D, and the immediate second base and third base constitute one CpG, while the $4^{th}$-$9^{th}$ bases contain one base G and the other bases are D, wherein D is A or T or G.

2. The method for high-throughput sequencing of methylated CpG island in trace DNA according to claim 1, wherein the 5' sequence of the primer A can be annealed to the adapter primer C.

3. The method for high-throughput sequencing of methylated CpG island in trace DNA according to claim 1, wherein the 5' sequence of the primer B can be annealed to the adapter primer D.

4. The method for high-throughput sequencing of methylated CpG island in trace DNA according to claim 1, wherein the 3' sequence of the primer B includes a relatively random annealing sequence having 5-15 bases in length, this sequence contains 0-15 bases C, 0-15 bases D, and 0-7 CpG, wherein D is A or T or G.

5. The method for high-throughput sequencing of methylated CpG island in trace DNA according to claim 1, wherein the 5' and 3' sequences of the primer B are connected by 4-20 bases D, wherein D is A or T or G.

6. The method for high-throughput sequencing of methylated CpG island in trace DNA according to claim 1, wherein the primer B is a single primer or a mixture of multiple primers.

7. The method for high-throughput sequencing of methylated CpG island in trace DNA according to claim 1, wherein the primer B is a mixture of the four primers consisting of the nucleotide sequences of SEQ ID Nos: 2, 3, 4 and 5.

8. The method for high-throughput sequencing of methylated CpG island in trace DNA according to claim 1, wherein the sequence of primer C consists of the nucleotide sequence of SEQ ID No: 6.

9. The method for high-throughput sequencing of methylated CpG island in trace DNA according to claim 1, wherein the sequence of primer D consists of the nucleotide sequence of SEQ ID No: 7.

* * * * *

SEQUENCE LISTING

<160> NUMBER OF SEQ ID NOS: 7

<210> SEQ ID NO 1
<211> LENGTH: 42
<212> TYPE: DNA
<213> ORGANISM: Artificial Sequence
<220> FEATURE:
<223> OTHER INFORMATION: the sequence is synthesized
<220> FEATURE:
<221> NAME/KEY: misc_feature
<222> LOCATION: (1)..(42)

<400> SEQUENCE: 1
tttccctaca cgacgctctt ccgatctcat ghhhhccgcg cg                         42

<210> SEQ ID NO 2
<211> LENGTH: 50
<212> TYPE: DNA
<213> ORGANISM: Artificial Sequence
<220> FEATURE:
<223> OTHER INFORMATION: the sequence is synthesized
<220> FEATURE:
<221> NAME/KEY: misc_feature
<222> LOCATION: (1)..(50)
<223> OTHER INFORMATION: d=a/t/g

<400> SEQUENCE: 2
gtgactggag ttcagacgtg tgctcttccg atctcatgdd dddddgcgd                  50

<210> SEQ ID NO 3
<211> LENGTH: 50
<212> TYPE: DNA
<213> ORGANISM: Artificial Sequence
<220> FEATURE:
<223> OTHER INFORMATION: the sequence is synthesized
<220> FEATURE:
<221> NAME/KEY: misc_feature
<222> LOCATION: (1)..(50)
<223> OTHER INFORMATION: d=a/t/g

<400> SEQUENCE: 3
gtgactggag ttcagacgtg tgctcttccg atctcatgdd ddddgdcgd                  50

<210> SEQ ID NO 4
<211> LENGTH: 50
<212> TYPE: DNA
<213> ORGANISM: Artificial Sequence
<220> FEATURE:
<223> OTHER INFORMATION: the sequence is synthesized
<220> FEATURE:
<221> NAME/KEY: misc_feature
<222> LOCATION: (1)..(50)
<223> OTHER INFORMATION: d=a/t/g

<400> SEQUENCE: 4
gtgactggag ttcagacgtg tgctcttccg atctcatgdd ddddgddcgd                 50

<210> SEQ ID NO 5
<211> LENGTH: 50
<212> TYPE: DNA
<213> ORGANISM: Artificial Sequence
<220> FEATURE:
<223> OTHER INFORMATION: the sequence is synthesized
<220> FEATURE:
<221> NAME/KEY: misc_feature
<222> LOCATION: (1)..(50)
<223> OTHER INFORMATION: d=a/t/g

```
<400> SEQUENCE: 5
gtgactggag ttcagacgtg tgctcttccg atctcatgdd dddgdddcgd          50

<210> SEQ ID NO 6
<211> LENGTH: 58
<212> TYPE: DNA
<213> ORGANISM: Artificial Sequence
<220> FEATURE:
<223> OTHER INFORMATION: the sequence is synthesized

<400> SEQUENCE: 6
aatgatacgg cgaccaccga gatctacact ctttccctac acgacgctct tccgatct    58

<210> SEQ ID NO 7
<211> LENGTH: 54
<212> TYPE: DNA
<213> ORGANISM: Artificial Sequence
<220> FEATURE:
<223> OTHER INFORMATION: the sequence is synthesized

<400> SEQUENCE: 7
caagcagaag acggcatacg agatctgatc gtgactggag ttcagacgtg tgct          54
```